United States Patent
Adem et al.

(10) Patent No.: US 10,702,525 B1
(45) Date of Patent: Jul. 7, 2020

(54) PYRIMIDINE DERIVATIVES AS ANTI-DIABETIC AGENTS

(71) Applicant: UNITED ARAB EMIRATES UNIVERSITY, Al Ain (AE)

(72) Inventors: Abdu Adem, Al Ain (AE); Shaikha S. Al Neyadi, Al Ain (AE); Ibrahim M. Abdu, Al Ain (AE); Alaa A. Salem, Al Ain (AE); Naheed Amir, Al Ain (AE)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 16/560,919

(22) Filed: Sep. 4, 2019

(51) Int. Cl.
C07D 239/42 (2006.01)
A61K 31/505 (2006.01)
A61P 3/10 (2006.01)
A61K 31/5377 (2006.01)

(52) U.S. Cl.
CPC ........ A61K 31/505 (2013.01); A61K 31/5377 (2013.01); A61P 3/10 (2018.01); C07D 239/42 (2013.01)

(58) Field of Classification Search
CPC .......................... C07D 239/42; C07D 413/04
See application file for complete search history.

(56) References Cited

U.S. PATENT DOCUMENTS

| | | | | |
|---|---|---|---|---|
| 6,080,750 | A * | 6/2000 | Hisaki | C07D 239/48 514/256 |
| 6,528,512 | B1 | 3/2003 | Gallagher et al. | |
| 7,001,910 | B1 | 2/2006 | Mourelle Mancini et al. | |
| 7,396,836 | B2 | 7/2008 | Harada et al. | |
| 7,790,729 | B2 | 9/2010 | Saavedra et al. | |
| 7,820,654 | B2 | 10/2010 | Pal et al. | |
| 8,653,111 | B2 | 2/2014 | Thede | |
| 8,906,902 | B2 | 12/2014 | Lunniss et al. | |
| 8,962,834 | B2 | 2/2015 | Baumann et al. | |
| 9,242,969 | B2 | 1/2016 | Barsanti et al. | |
| 2005/0032849 | A1 * | 2/2005 | Phadke | C07C 335/12 514/357 |
| 2005/0272788 | A1 * | 12/2005 | Acton, III | C07D 413/04 514/381 |
| 2008/0176866 | A1 | 7/2008 | Jautelat | |
| 2008/0249115 | A1 * | 10/2008 | Cuttitta | A61K 31/194 514/263.37 |
| 2009/0036448 | A1 | 2/2009 | Sekiguchi et al. | |
| 2012/0045441 | A1 * | 2/2012 | Sunday | A61K 31/505 424/141.1 |
| 2013/0280270 | A1 * | 10/2013 | Sunday | A61K 31/505 424/152.1 |
| 2014/0336159 | A1 * | 11/2014 | Clarke | A61K 9/0075 514/171 |
| 2015/0087827 | A1 | 3/2015 | Militzer et al. | |
| 2015/0297591 | A1 * | 10/2015 | Sunday | A61K 31/505 424/152.1 |

FOREIGN PATENT DOCUMENTS

EP 1464335 A2 * 10/2004 ............ C07D 239/48
FR 2856401 A1 12/2004

(Continued)

OTHER PUBLICATIONS

M. Yanai et al., 94 Yakugaku Zasshi, 1503-1514 (1974) (Year: 1974).*
S. Zhou et al., 182 American Journal of Pathology, 1248-1254 (2013) (Year: 2013).*
Wacker et al. "Discovery of 5-Chloro-4-((1-(5-chloropyrimidin-2-yl)piperidin-4-yl)oxy)-1-(2-fluoro-4-(methylsulfonyl)phenyl)pyridin-2 (1 H)-one (BMS-903452), an Antidiabetic Clinical Candidate Targeting GPR119." Journal of medicinal chemistry 57.18 (2014): 7499-7508.
Knudsen et al., "Small-molecule agonists for the glucagon-like peptide 1 receptor", Proc Natl Acad Sci U S A 2007. 104: p. 937-942.
Teng et al., "Small molecule ago-allosteric modulators of the human glucagon-like peptide-1 (hGLP-1) receptor", Bioorg Med Chem Lett, 2007. 17: p. 5472-5478. (Abstract only).

(Continued)

*Primary Examiner* — Alexander R Pagano
(74) *Attorney, Agent, or Firm* — Richard C. Litman; Nath, Goldberg & Meyer (57) ABSTRACT

The pyrimidine derivatives as anti-diabetic agents are chloropyrimidinyl derivatives having the general formula of compound 81, wherein $R_1$ is $-N(CH3)CH_2CH_2OH$ (compound 81c) or $-N(H)CH_2CH_2OH$ (compound 81f) or the general formula of compound 82, wherein $R_2$ is $-N(CH_3)CH_2CH_2OH$ (compound 82c) or $-N(CH_2CH_2)_2O$ (compound 82d), as follows:

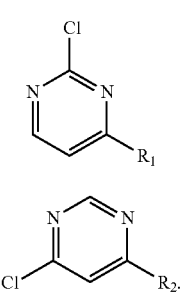

The derivatives may be used for treating diabetes in humans or animals and have demonstrated efficacy, specifically in treating type 2 diabetes. Two methods of synthesizing the pyrimidine derivatives are described herein. The method using microwaves (Method B) is a green method that can provide high yields in a short time and with high purity. The compounds act as GLP-1 receptor agonists and are more potent than conventional drugs. As such, the compounds may be used in lower doses, and, hence, have fewer side effects.

2 Claims, 6 Drawing Sheets

(56) References Cited

FOREIGN PATENT DOCUMENTS

| JP | 2006124387 A | * | 5/2006 | |
|---|---|---|---|---|
| WO | WO-0058305 A1 | * | 10/2000 | ........... C07D 487/04 |
| WO | WO-0136416 A1 | * | 5/2001 | ........... C07D 473/34 |
| WO | 2004074287 A1 | | 9/2004 | |
| WO | WO-2004074287 A1 | * | 9/2004 | ........... C07D 213/82 |
| WO | WO-2005095357 A2 | * | 10/2005 | ........... C07D 413/12 |
| WO | WO-2007105023 A1 | * | 9/2007 | ........... C07D 241/40 |
| WO | WO 2019238424 A1 | * | 12/2019 | |

OTHER PUBLICATIONS

Deng et al., "The highly potent and selective dipeptidyl peptidase IV inhibitors bearing a thienopyrimidine scaffold effectively treat type 2 diabetes". Eur. J. Med. Chem, 2010. 46(1): p. 71-76. (Abstract only).

Bahekar et al., "Synthesis and antidiabetic activity of 3,6,7-trisubstituted-2-(1Himidazol-2-ylsulfanyl)quinoxalines and quinoxalin-2-yl isothioureas", Arch Pharm (Weinheim) 2007. 340: p. 359-366. (Abstract only).

Irwin, et al., "Insulin-releasing and metabolic effects of small molecule GLP-1 receptor agonist 6,7-dichloro-2-methylsulfonyl-3-N-tert-butylaminoquinoxaline", Eur J Pharmacol 2010. 628: p. 268-273. (Abstract only).

Chen et al., "A nonpeptidic agonist of glucagon-like peptide 1 receptors with efficacy in diabetic db/db mice", Proc Natl Acad Sci U S A 2007. 104: p. 943-948.

"2-[(2-chloro-4-pyrimidinyl)methylamino]-ethanol", PubChem at https://pubchem.ncbi.nlm.nih.gov/ database, printed on Jul. 18, 2019 (10 pages).

"2-[2-chloropyrimidin-4-yl)-methylamino]ethanol", Aurora Fine Chemicals, printed on Jul. 18, 2019 from http://online.aurorafinechemicals.com/info?ID=A05.897.286, 1 sheet.

"Product ID: F8882-9509", Lifechemicals Store, printed on Jul. 18, 2019 from https://shop.lifechemicals.com/1/F8882-9509, 2 sheets.

"AKos Samples AKOS002663362", AKos Samples Germany, printed Jul. 18, 2019 from http://akoscompounds.de/catalogue/?IDNUMBERS=AKOS002663362, 1 sheet.

"2-[2-Chloropyrimidin-4-yl)amino]ethanol", PubChem at https://pubchem.ncbi.nlm.nih.gov/ database, printed on Jul. 18, 2019 (12 pages).

"2-[6-Chloro-4-pyrimidinyl)(methyl)amino]-1-ethanol", printed Jul. 19, 2019 from https://www.chembook.com/ChemicalProductProperty_EN_CB02482307.htm, 2 sheets.

"4-(6-Chloropyrimidin-4-yl)morpholine", PubChem at https://pubchem.ncbi.nlm.nih.gov/ database, printed on Jul. 19, 2019 (15 pages).

"4-(6-chloropyramidin-4-yl)morpholine", Sigma-Aldrich, printed on Jul. 19, 2019 from www.sigmaaldrich.com online catalog, 3 sheets.

* cited by examiner

PYRIMIDINE DERIVATIVES AS ANTI-DIABETIC AGENTS

BACKGROUND

1. Field

The disclosure of the present patent application relates to chloro-pyrimidine derivatives exhibiting anti-diabetic activity, and particularly to pyrimidine derivatives as anti-diabetic agents for treating type 2 diabetes by lowering fasting glucose levels and stimulating insulin secretion.

2. Description of the Related Art

Diabetes, and particularly diabetes type 2, is one of the most common diseases today. This prevalence drives an increasing demand for novel compounds that have good potency with fewer side effects in treating patients for diabetes.

In healthy human beings, oral glucose elicits a considerably higher insulin secretory response than does intravenous glucose, referred to as the incretin effect. The incretin effect is substantially reduced or even lost in patients with type 2 diabetes. Therefore, the development of incretin-based therapeutics may be an effective strategy to restore normal islet function in type 2 diabetes mellitus.

Glucose-dependent insulinotropic polypeptide (GIP) and Glucagon-like peptide-1 (GLP-1) are incretin hormones. GIP is synthesized in duodenal and jejunal enteroendocrine K cells in the proximal small bowel. Glucagon-like peptide-1 (GLP-1) is released from intestinal L cells following nutrient consumption. GLP-1 potentiates the glucose-induced secretion of insulin from pancreatic beta cells, increases insulin expression, inhibits beta-cell apoptosis, promotes beta-cell neogenesis, reduces glucagon secretion, delays gastric emptying, promotes satiety, and increases peripheral glucose disposal. These multiple effects have generated a great deal of interest in the discovery of long-lasting agonists of the GLP-1 receptor (GLP-1) in order to treat type 2 diabetes. GLP-1 acts by binding to G-protein-coupled receptors (GPCRs). These receptors are members of the class B/II family of seven transmembrane GPCRs. Activation of both incretin receptors on β cells leads to rapid increases in levels of cAMP and intracellular calcium, followed by insulin exocytosis, in a glucose-dependent manner.

In type 2 diabetes mellitus, homeostasis of postprandial glucose is impaired by the dysregulation of insulin's secretion and high glucagon levels. In addition, impairment of incretin results in reduced secretion of glucagon like peptide-1 (GLP-1) and subsequent progression of pancreatic islet dysfunction. Since GLP-1 action remains relatively preserved in diabetic patients, pharmacological efforts directed at potentiation of incretin action for the treatment of type 2 diabetes may focus on developing and identifying GLP-1 receptor agonists.

Thus, pyrimidine derivatives as anti-diabetic agents solving the aforementioned problems are desired.

SUMMARY

The pyrimidine derivatives as anti-diabetic agents are chloropyrimidinyl derivatives having the general formula of compound 81, wherein $R_1$ is —N(CH3)CH$_2$CH$_2$OH (compound 81c) or —N(H)CH$_2$CH$_2$OH (compound 81f) or the general formula of compound 82, wherein $R_2$ is —N(CH$_3$)CH$_2$CH$_2$OH (compound 82c) or —N(CH$_2$CH$_2$)$_2$O (compound 82d), as follows:

The derivatives may be used for treating diabetes in humans or animals and have demonstrated efficacy, specifically in treating type 2 diabetes, as will be discussed in the following examples. Two methods of synthesizing the pyrimidine derivatives are described herein. The method using microwaves (Method B) is a green method that can provide high yields in a short time and with high purity. The compounds act as GLP-1 receptor agonists and are more potent than conventional drugs. As such, the compounds may be used in lower doses and, hence, have fewer side effects.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The pyrimidine derivatives as anti-diabetic agents are chloropyrimidinyl derivatives having the general formula of compound 81, wherein $R_1$ is —N(CH3)CH$_2$CH$_2$OH (compound 81c) or —N(H)CH$_2$CH$_2$OH (compound 81f), or having the general formula of compound 82, wherein $R_2$ is —N(CH$_3$)CH$_2$CH$_2$OH (compound 82c) or —N(CH$_2$CH$_2$)$_2$O (compound 82d), as follows:

The derivatives may be used for treating diabetes in humans or animals and have demonstrated efficacy, specifically in treating type 2 diabetes, as will be discussed in the following examples. Two methods of synthesizing the pyrimidine derivatives are described herein. The method using microwaves (Method B) is a green method that can provide high yields in a short time and with high purity. The compounds act as GLP-1 receptor agonists and are more potent than conventional drugs. As such, the compounds may be used in lower doses and, hence, have fewer side effects.

In one embodiment, the pyrimidine derivatives may be synthesized according to a method referred to as "method A", in which a dichloropyrimidine is mixed with sodium carbonate in ethanol. An amine in ethanol solution is added dropwise to form a reaction mixture, and the reaction mixture is refluxed. In another embodiment, referred to as "method B", a dichloropyrimidine is mixed with an amine and irradiated by microwave irradiation in the presence of N,N-diisopropylethylamine (DIPEA).

The pyrimidine derivatives may be effective in decreasing blood sugar. These compounds may be administered to a patient in any suitable pharmaceutical formulation, with any suitable pharmaceutical excipients known in the industry, for administration to a patient in any suitable manner as generally known in the industry that may be determined or selected by the medical practitioner treating the patient.

Figure 5A:
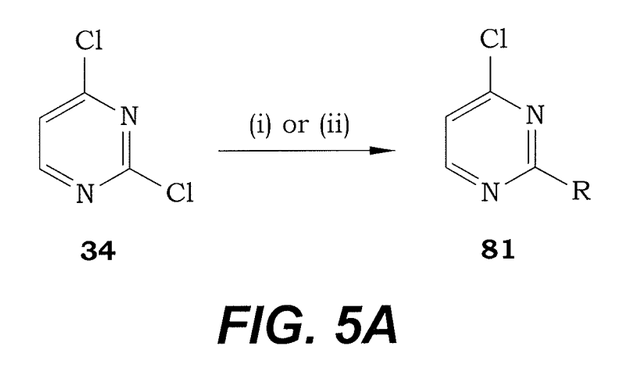
FIG. 5A is a reaction scheme for synthesizing compounds 81c and 81f from 2,4-dichloropyrimidine (compound 34), which may be done according to (i) Method A or (ii) Method B.
Figure 5B:
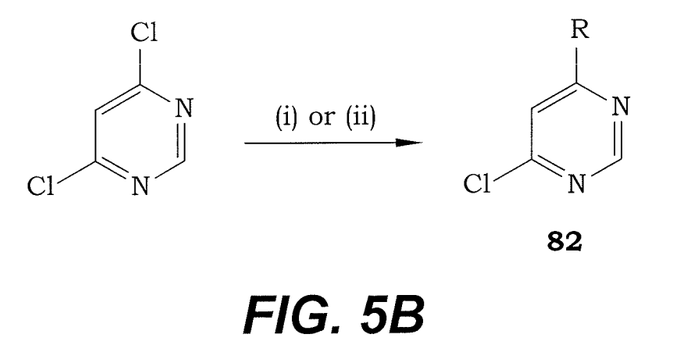
FIG. 5B is a reaction scheme for synthesizing compounds 82c and 82d from 4,6-dichloropyrimidine, which may be done according to (i) Method A or (ii) Method B.

According to an embodiment, the pyrimidine derivatives include mono-substituted 2,4-dichloropyrimidines, such as compounds 81c and 81f or a pharmaceutically acceptable salt thereof (FIG. 5A) and mono-substituted 4,6-dichloropyrimidines, such as compounds 82c and 82d, or a pharmaceutically acceptable salt thereof (FIG. 5B).

According to an embodiment, the non-peptide pyrimidine derivatives include at least one of:

or a pharmaceutically acceptable salt thereof.

As described herein, in vitro and in vivo studies revealed that compounds 81c, 81f, 82c, and 82d increase glucose-stimulated insulin release from βTC6 cells compared to basal controls, and also decrease fasting blood glucose levels in diabetic rat models. Accordingly, compounds 81c, 81f, 82c and 82d are able to increase glucose-stimulated insulin secretion, and thereby prevent hyperglycemia. Pharmaceutical compositions comprising one or more of the compounds and at least one pharmaceutically acceptable excipient may be used to effectively treat type 2 diabetes and related disorders.

The present disclosure is illustrated by the following examples.

Example 1

Synthesis of Compound 81c and Compound 81f by Method A

In separate experiments, compounds 81c,f were prepared by first forming a reaction mixture of 2,4-dichloropyrimidine (1.0 mmol, 0.148 g) and sodium carbonate (2.0 mmol, 0.211 g) in ethanol, followed by dropwise addition of an ethanolic solution of the appropriate amine (2-(methylamino)ethanol for compound 81c, 2-aminoethanol for compound 81f; 1.0 mmol) under reflux. The reaction mixture was refluxed for 2-8 hrs. The solvent was removed under reduced pressure. The collected residue was dissolved in 20.0 ml ethyl acetate, washed with water (2×20 ml). The organic layer was dried over anhydrous MgSO$_4$, filtered and concentrated under reduced pressure, then purified on a silica gel column using ethyl acetate-hexane (1:1) to afford the desired products.

Example 2

Synthesis of Compound 81c and Compound 81f by Method B

In separate experiments, compounds 81c and 81f were obtained by reacting 2,4-dichloropyrimidine (1.0 mmol, 0.148 g) with the appropriate amines (2-(methylamino)

ethanol for compound 81c, 2-aminoethanol for compound 81f; 1.0 mmol) in ethanol (2-3 ml) at 0° C. in the presence of N,N-diisopropylethylamine (DIPEA, 1.1 mmol) under microwave irradiation for 10-20 min. The progress of reaction was monitored by TLC. Ethyl acetate (10.0 ml) was added to the reaction mixture, and the pH was adjusted to 7-7.5 using HCl (6.0 M). The mixture was washed with saturated aqueous solution of $NaHCO_3$. The organic layer was dried over anhydrous $MgSO_4$. The excess solvent was removed under reduced pressure, and the obtained residue was further purified by column chromatography using ethyl acetate-hexane (1:1) to afford the final products 81c and 81f in good yields. See Table 1.

Example 3

Characterization of 2-[(2'-Chloropyrimidin-4'-yl)-methylamino]ethanol (Compound 81c)

Yield 87% (Method A), 89% (Method B), Off-white solid, mp 136° C.; IR (KBr, cm$^{-1}$): 3394 (O—H), 3115 (C—H, aromatic), 2915 (C—H, aliphatic); $^1$H-NMR (400 MHz, DMSO-d$_6$) δ ppm: 3.13 (s, 3H, $CH_3$), 3.30 (s, OH, exchanges with $D_2O$), 3.74 (m, 2H, $CH_2$), 3.85-3.88 (m, 2H, $CH_2$), 6.37 (d, 1H, $H_5$-pyrimidine, J=5.9 Hz), 7.96 (d, 1H, $H_6$-pyrimidine, J=6.0 Hz); $^{13}$C-NMR (100 MHz, DMSO-d$_6$) δ ppm: 162.9 (C4-pyrimidine), 159.5 (C6-pyrimidine), 157.4 (C2-pyrimidine), 101.6 (C5-pyrimidine), 60.9 ($CH_2$), 52.7 ($CH_2$), 37.1 ($CH_2$); Anal. Calcd for $C_7H_{10}ClN_3O$: C, 44.81; H, 5.37; N, 22.40; Found: C, 45.20; H, 5.88; N, 22.96.

Example 4

Characterization of 2-[(2'-Chloropyrimidin-4'-yl) amino]ethanol (Compound 82f)

Yield 68% (Method A), 81% (Method B), pale yellow solid, mp 116-117° C.; IR (KBr, cm$^{-1}$): 3276 (N—H, O—H), 3095 (C—H, aromatic), 2869 (C—H, aliphatic), 1511 (N—H bending); $^1$H-NMR (400 MHz, DMSO-d$_6$) δ ppm: 3.41-3.48 (m, 5H, 2$CH_2$, OH, exchanges with $D_2O$), 6.43 (d, 1H, $H_5$-pyrimidine, J=5.6 Hz), 7.82 (d, 1H, $H_6$-pyrimidine, J=5.6 Hz), 7.92 (s, 1H, NH, exchanges with $D_2O$); $^{13}$C-NMR (100 MHz, DMSO-d$_6$) δ ppm: 163.9 (C2-pyrimidine), 160.1 (C6-pyrimidine), 155.5 (C4-pyrimidine), 105.6 (C5-pyrimidine), 59.5 ($CH_2$), 42.9 ($CH_2$); Anal. Calcd for $C_6H_8ClN_3O$: C, 41.51; H, 4.64; N, 24.21; Found: C, 42.93; H, 5.01; N, 23.37.

Example 5

Synthesis of Compound 82c and Compound 82d by Method A

In separate experiments, compounds 82c and 82d were prepared by first forming a reaction mixture of 4,6-dichloropyrimidine (1.0 mmol, 0.148 g), sodium carbonate (2.0 mmol, 0.211 g) in ethanol, and further dropwise addition of an ethanolic solution of the appropriate amine (2-(methylamino)ethanol for compound 82c and morpholine for compound 82d; 1.0 mmol) under reflux. The reaction mixture was refluxed for 2-8 hrs. The solvent was removed under reduced pressure. The collected residue was dissolved in 20.0 ml ethyl acetate, and washed with water (2×20 ml). The organic layer was dried over anhydrous $MgSO_4$, filtered and concentrated under reduced pressure, then purified on a silica gel column using ethyl acetate-hexane (1:1) to afford the desired products.

Example 6

Synthesis of Compound 82c and Compound 82d by Method B

In separate experiments, compounds 82c and 82d were obtained by reacting 4,6-dichloropyrimidine (1.0 mmol, 0.148 g) with the appropriate amine (2-(methylamino)ethanol for compound 82c and morpholine for compound 82d; 1.0 mmol) in ethanol (2-3 ml) at 0° C. in the presence of N,N-diisopropylethylamine (DIPEA, 1.1 mmol) under microwave irradiation for 10-20 min. The progress of reaction was monitored by TLC. Ethyl acetate (10.0 ml) was added to the reaction mixture, and the pH was adjusted to 7-7.5 using HCl (6.0 M). The mixture was washed with saturated aqueous solution of $NaHCO_3$. The organic layer was dried over anhydrous $MgSO_4$. The excess solvent was removed under reduced pressure, and the obtained residue was further purified by column chromatography using ethyl acetate-hexane (1:1) to afford the final products 82c and 82d, respectively in good yields. See Table 1.

TABLE 1

| | Comparison of Methods A and B - Time and Yield | | | |
|---|---|---|---|---|
| | Method A | | Method B | |
| Compound | Time (min) | Yield % | Time (min) | Yield % |
| 81c | 210 min | 87 | 10 min | 89 |
| 81f | 180 min | 68 | 10 min | 81 |
| 82c | 210 min | 86 | 10 min | 93 |
| 82d | 150 min | 85 | 7 min | 95 |

Example 7

Characterization of 2-[(6'-Chloropyrimidin-4'-yl)(methylamino)]ethanol (Compound 82c)

Yield 86% (Method A), 93% (Method B), white solid, mp 138° C.; IR (KBr, 3390 (O—H), 3100 (C—H, aromatic), 2898 (aliphatic C—H); $^1$H-NMR (400 MHz, CDCl$_3$) δ ppm: 2.87 (s, OH, exchanges with $D_2O$), 3.10 (s, 3H, $CH_3$), 3.77 (m, 2H, $CH_2$), 3.84 (m, 2H, $CH_2$), 6.46 (1H, $H_5$-pyrimidine), 8.32 (s, 1H, $H_2$-pyrimidine); $^{13}$C-NMR (100 MHz, CDCl$_3$) δ ppm: 162.9 (C4-pyrimidine), 159.5 (C6-pyrimidine), 157.4 (C2-pyrimidine), 101.6 (C5-pyrimidine), 61.0 ($CH_2$), 52.7 ($CH_2$), 37.1 ($CH_3$); Anal. Calcd for $C_7H_{10}ClN_3O$: C, 44.81; H, 5.37; N, 22.40; Found: C, 44.93; H, 5.44; N, 22.71.

Example 8

Characterization of 4-(6'-Chloropyrimidin-4'-yl)morpholine (Compound 82d)

Yield 85% (Method A), 95% (Method B), pale yellow solid, mp 153-154° C.; IR (KBr, cm$^{-1}$): 3069 (C—H, aromatic), 2968 (aliphatic C—H), 1260 (C—O—C, ether linkage); $^1$H-NMR (400 MHz, CDCl$_3$) δ ppm: 3.62-3.78 (m, 8H, morpholine), 6.49 (s, 1H, $H_5$-pyrimidine), 8.38 (s, 1H, H$_2$-pyrimidine); $^{13}$C-NMR (100 MHz, CDCl$_3$) δ ppm: 162.7 (C4-pyrimidine), 160.3 (C6-pyrimidine), 158.1 (C2-pyrimidine), 101.5 (C5-pyrimidine), 66.3 (C3'-morpholine), 44.2 (C2'-morpholine); Anal. Calcd for C$_8$H$_{10}$ClN$_3$O: C, 48.13, H, 5.05; N, 21.05; Found: C, 48.30; H, 5.08; N, 21.33.

Example 9

Effects of Exemplary Pyrimidine Derivatives on Fasting Glucose Levels of Diabetic Rat Model Rats injected with Streptozotocin (STZ) showed significant increases in plasma glucose level and kidney weight along with decreases in serum insulin and body weight in comparison with non-diabetic rats. These symptoms indicate the development of diabetes characterized by chronic and persistently elevated plasma glucose level. STZ induces diabetes by selectively destroying the insulin producing pancreatic endocrine cells. Decreased body weight in STZ-induced diabetic rats is believed to be caused by dehydration, and by breakdown and catabolism of fats and proteins. Increased catabolic reactions upon administering STZ result in muscle wasting, and subsequently, body weight loss.

Figure 1A:
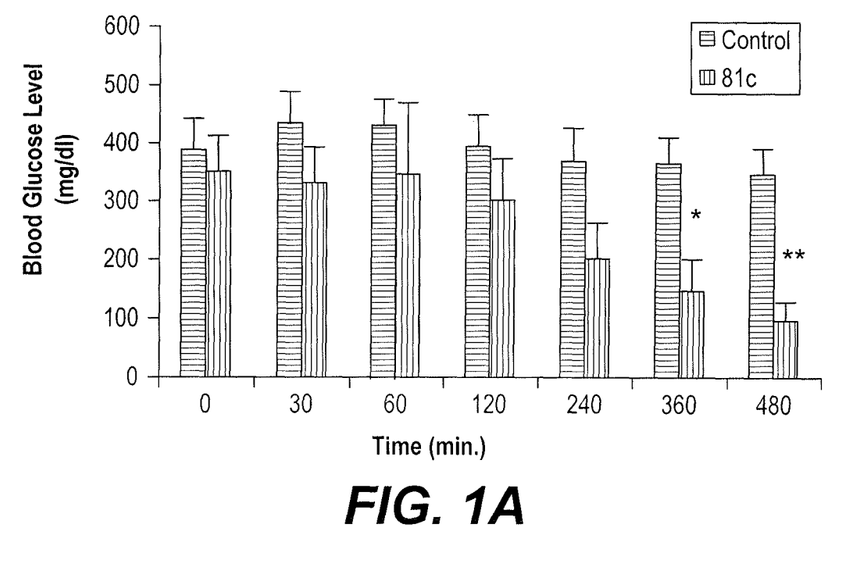
FIGS. 1A, 1B, 1C, and 1D are charts depicting results of tests demonstrating the anti-hyperglycemic effect of exemplary compounds 81c, 81f, 82c, and 82d, respectively, on the fasting blood glucose level of Streptozotocin-injected (STZ) diabetic rats as compared to a STZ diabetic rat control group.
Figure 1B:
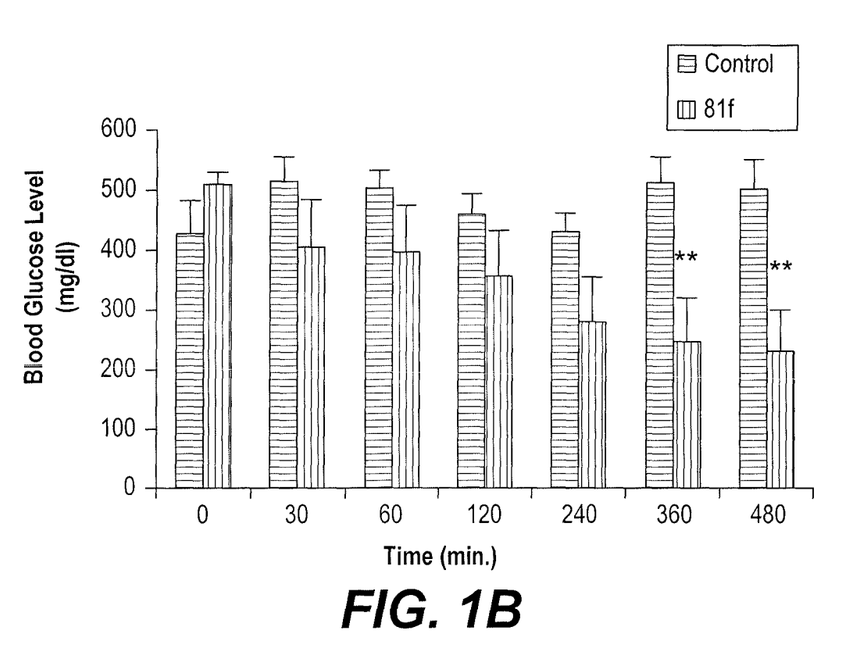
Figure 1C:
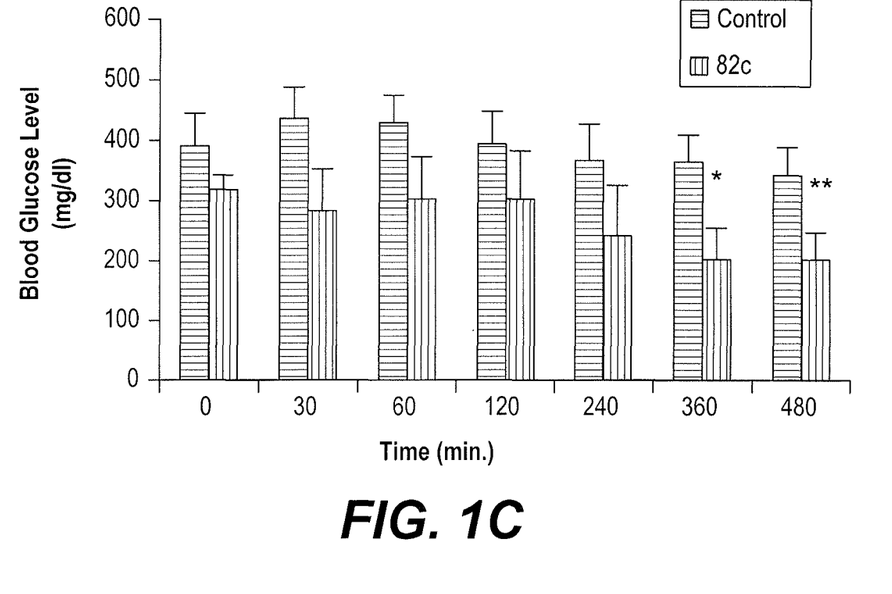
Figure 1D:
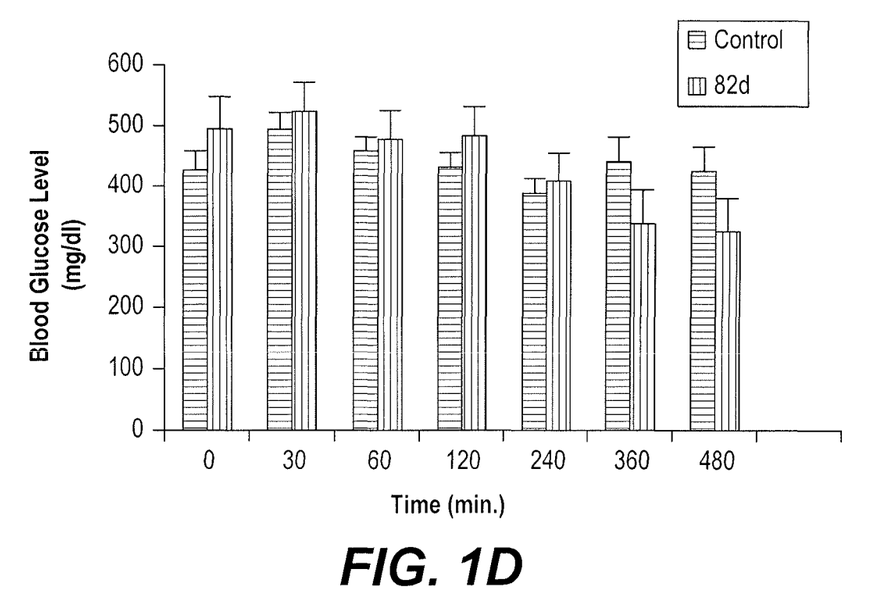

Compounds 81c, 81f, 82c, and 82d, synthesized as described in Examples 1, 2, 5, and 6 were orally administrated to the treated groups of diabetic rats at a dose of 1.0 µM/kg. Fasting glucose levels in treated and control rat blood were followed over 8.0 hours. Diabetic rats treated with compounds 81c and 81f showed significant reduction in blood glucose level 6 and 8 hours after treatment compared to control diabetic groups. As seen in FIGS. 1A and 1B, compounds 81c and 81f significantly reduce blood glucose levels. However, compound 81c shows high potency in reducing the blood glucose level at 8 hours. Compounds 82c and 82d were also tested in vivo (FIGS. 1C, 1D). Compound 82d reduced blood glucose levels, but only compound 82c showed statistically significant reduction in blood glucose level 6 and 8 hours after treatment compared to diabetic control animals (FIG. 1C). In FIGS. 1A-1D the results are means±SEM, where n=6 rats; *P<0.05, P<0.01, and *P<0.001 vs. the STZ diabetic control group.

Example 10

Figure 2:
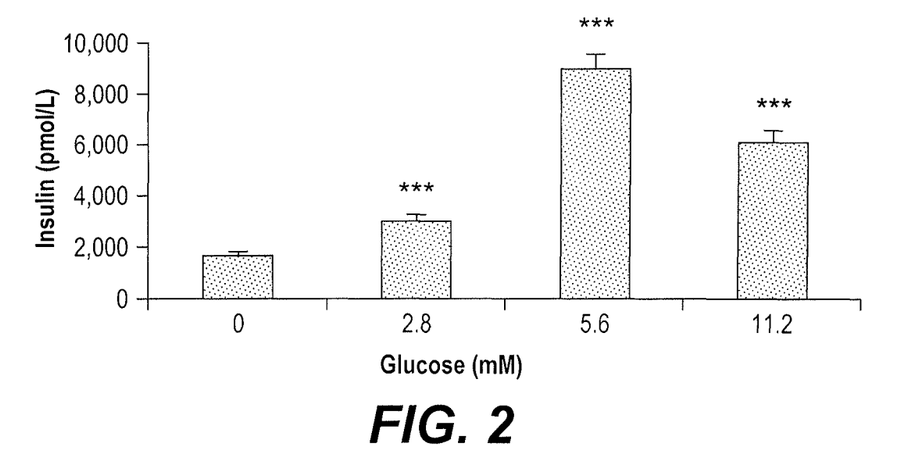
FIG. 2 is a chart showing the glucose response curve (insulin secretion in picomoles per liter [pmol/L] as a function of glucose concentration [millimolar, or mM]) of the murine βTC6 cell line in the absence of drugs.

Effects of Exemplary Pyrimidine Derivatives on Insulin Secretion from βTC6 Cell Line Secretion of insulin by βTC6 cells was measured using the high range insulin Sandwich ELISA kit. FIG. 2 shows the glucose response curve of the βTC6 cell in the absence of drugs. The 2.8 mM glucose provoked a mild insulin response of around 3 nMol, and was chosen as the glucose concentration used in testing the reference drug, exenatide, as well as the pyrimidine derivative compounds that showed significant anti-diabetic in vivo effects in rats, as above (FIGS. 1A-1D).

Figure 3A:
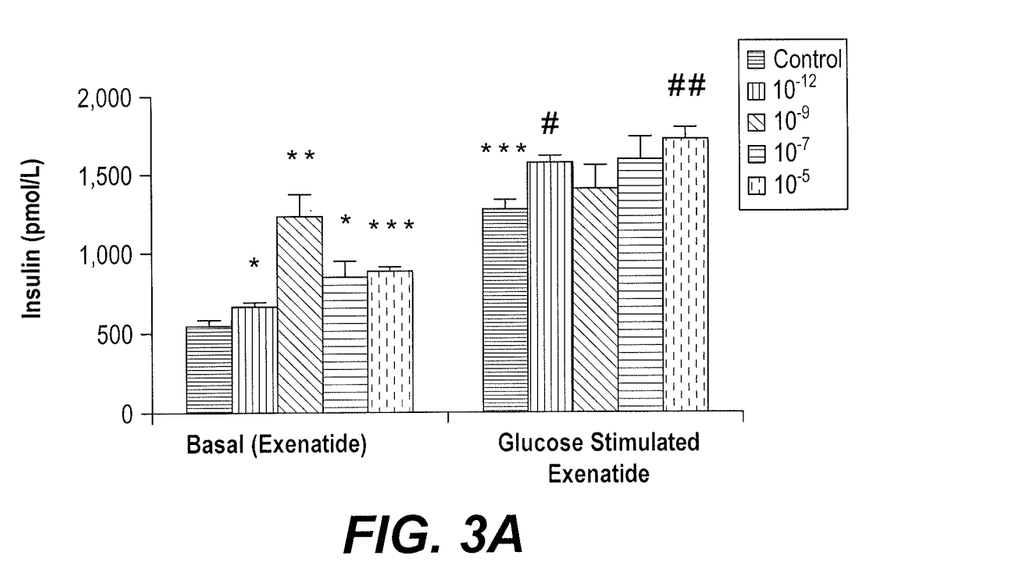
FIGS. 3A, 3B, 3C, and 3D are charts showing the effects of reference drug exenatide ($10^{-12}$-$10^{-5}$ M) and exemplary compounds 81c, 81f and 82c ($10^{-15}$-$10^{-9}$ M), respectively, on insulin secretion in βTC6 cells in the absence (basal) and in the presence of 2.8 mM glucose concentration.
Figure 3B:
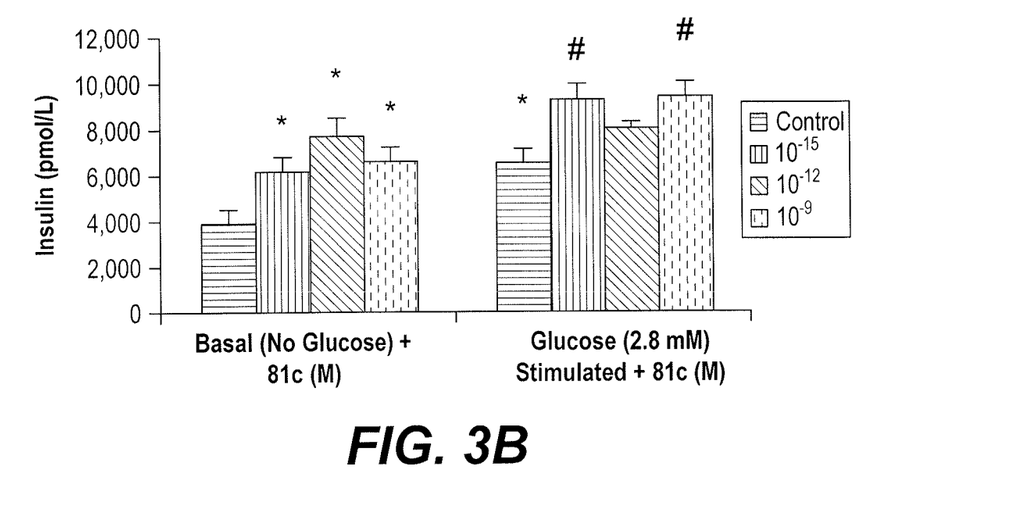
Figure 3C:
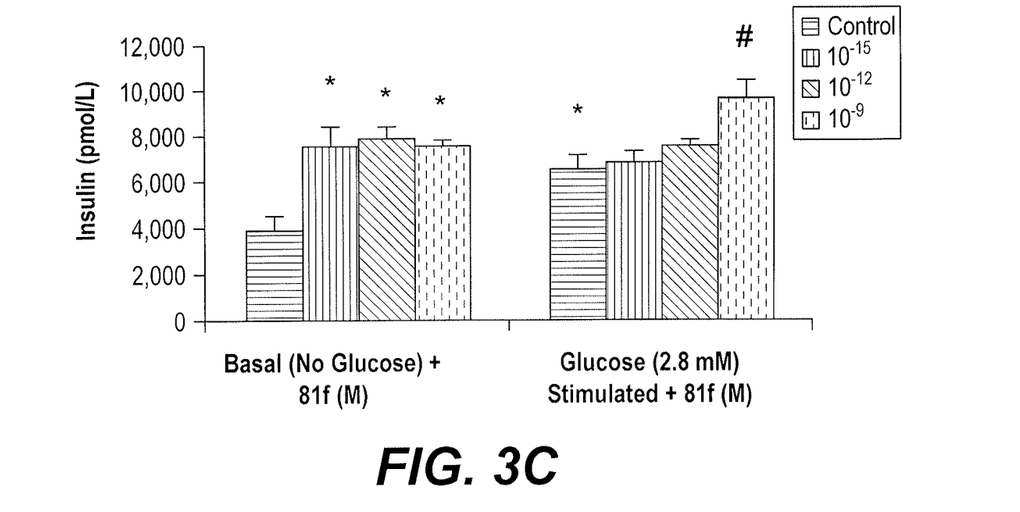
Figure 3D:
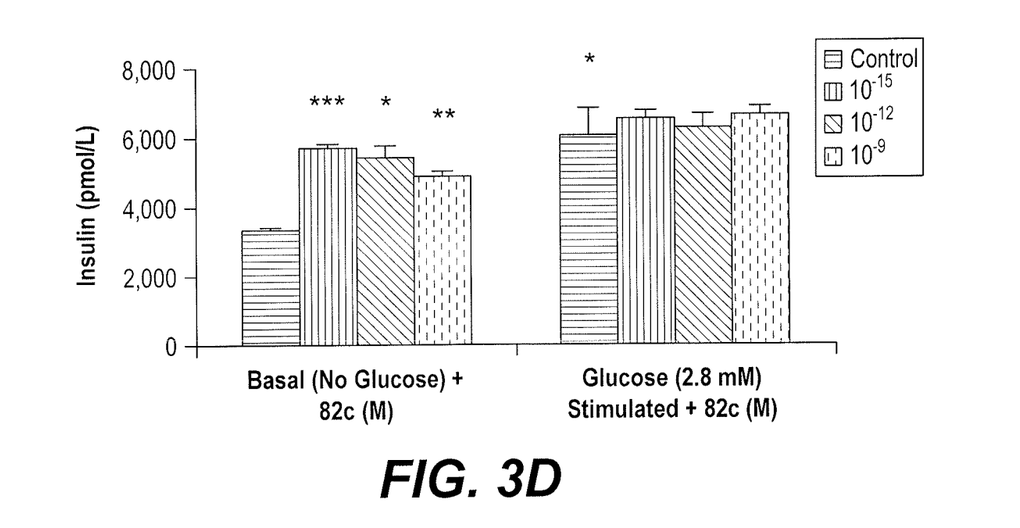

Exenatide treatment of βTC6 cells significantly increased insulin secretion compared to basal secretion. Moreover, in the presence of 2.8 mM glucose, exenatide significantly increased insulin secretion at $10^{-9}$ M and $10^{-12}$ M compared to untreated controls (i.e., 2.8 mM glucose alone) (FIG. 3A). FIGS. 3B-3D show the effects of the most potent in vitro pyrimidine derivatives 81c, 81f and 82c at $10^{-15}$ M, $10^{-12}$ M, and $10^{-9}$ M concentrations on insulin secretion in the absence and in the presence of 2.8 mM glucose. In the absence of glucose, compounds 81c, 81f and 82c at concentrations of $10^{-15}$ M, $10^{-12}$ M, and $10^{-9}$ M significantly stimulated insulin secretions, compared to the basal control. In the presence of 2.8 mM glucose, compounds 81c, 81f and 82c at concentrations of $10^{-15}$ M, $10^{-12}$ M, and $10^{-9}$ M stimulated insulin secretion significantly compared to basal insulin secretion, as well as insulin secretion in the presence of glucose. In FIGS. 3A-3D, the results are means of triplicates ±SEM, where *P<0.05, P<0.01, and *P<0.001 from relative basal control and #*P<0.05, ## P<0.01, and ### P<0.001 from glucose 2.8 mM.

Taken together, the in vivo and in vitro results indicate that compound 81c is the most potent anti-diabetic compound, followed by 81f and 82c, respectively. Compound 81c shows comparable effects to exenatide in insulin secretion from the βTC6 cell line.

In general, the compounds of formula 81 gave higher responses than those of formula 82. Compounds 81c, 81f and 82c, in which a chlorine atom of a dichloropyrimidine at position 4 is replaced by 2-(methylamino)ethanol or 2-aminoethanol (FIG. 5A) significantly increases the magnitude of the response, suggesting that the hydrogen bond donor in this location increases efficacy, and that the length of the linker affects binding to the ago-allosteric binding site of the GLP-1 receptor.

Example 11

Glucose Uptake Assay

Figure 4:
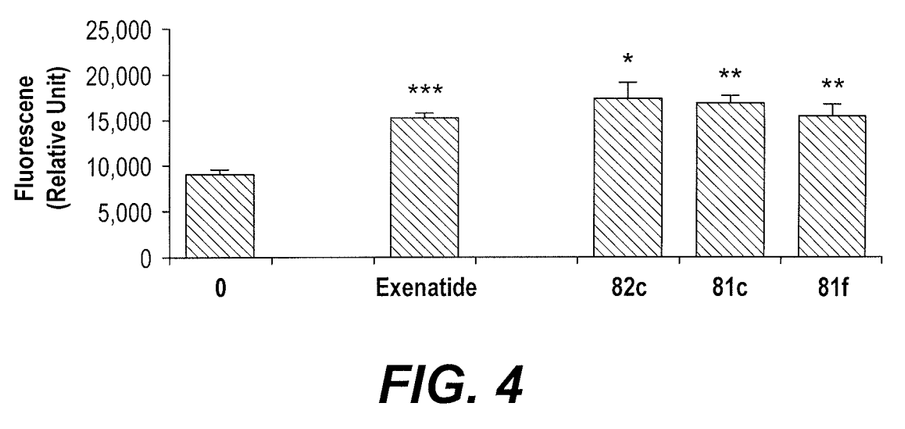
FIG. 4 is a chart showing the effects of the exemplary compounds 81c, 81f and 82c, and the reference drug exenatide, (10 μM) on glucose uptake in murine βTC6 cells.

The glucose uptake assay was performed with a cell-based assay kit by incubating 450 µM 2-[N-(7-nitrobenz-2-oxa-1,3-diaxol-4-yl)amino]-2-deoxyglucose (2-NBDG, a fluorescently labelled deoxyglucose analog) and a 10 µM sample of the reference drug or the test compound with βTC6 cells for ten minutes and subsequently measuring the fluorescence at excitation and emission wavelengths of 485 nm and 535 nm, respectively, with a TECAN infinite M200 micro plate reader. The results of the in vitro glucose uptake study indicate that the compounds 81c, 81f, and 82c were found to exhibit remarkable potential to flush glucose into the βTC6 cells as compared to the standard reference, exenatide (FIG. 4). In FIG. 4, the results are means of triplicates ±SEM, where *P<0.05, P<0.01, and *P<0.001 vs. control (zero concentration), and #*P<0.05, ## P<0.01, and ### P<0.001 vs. reference drug (Exenatide).

While not wishing to be bound by theory, molecular docking studies suggest that the mechanism for anti-diabetic action by the compounds 81c, 81f, 82c, and 82d may be that these pyrimidine derivatives may act as GLP-1 receptor agonists, with allosteric binding to the receptor and consequent stimulation of insulin production and uptake of glucose in the beta cells while not stimulating glucagon release. Consequently, the compounds 81c, 81f, 82c, and 82d appear to be suitable candidates as anti-diabetic agents in a pharmaceutical composition with a suitable excipient for oral delivery.

It is to be understood that the pyrimidine derivatives as anti-diabetic agents are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of treating a type 2 diabetes, comprising administering a therapeutically effective amount of compound 81c, or a pharmaceutically acceptable salt thereof, or a pharmaceutical composition thereof to a patient in need thereof:

81c

2. A method of treating a type 2 diabetes, comprising administering a therapeutically effective amount of compound 82c, or a pharmaceutically acceptable salt thereof, or a pharmaceutical composition thereof to a patient in need thereof:

82c

* * * * *